(12) United States Patent
Fearnside et al.

(10) Patent No.: US 6,575,922 B1
(45) Date of Patent: Jun. 10, 2003

(54) ULTRASOUND SIGNAL AND TEMPERATURE MONITORING DURING SONO-THROMBOLYSIS THERAPY

(75) Inventors: Jim Fearnside, Lexington, MA (US); Al Kyle, Andover, MA (US)

(73) Assignee: Walnut Technologies, Boston, MA (US)

( * ) Notice: Subject to any disclaimer, the term of this patent is extended or adjusted under 35 U.S.C. 154(b) by 163 days.

(21) Appl. No.: 09/691,471

(22) Filed: Oct. 17, 2000

(51) Int. Cl.[7] .............................. A61H 1/00; A61H 1/02; A61H 5/00; A61N 1/30

(52) U.S. Cl. ............................................. 601/2; 604/21

(58) Field of Search .............................. 604/22, 65, 67, 604/104, 158, 164, 508; 600/467, 471; 606/108, 198; 601/2

(56) References Cited

PUBLICATIONS

Article: Enhancement of Thrombolysis by external ultra-sound; Huai Luo, et al (From the Division of Cardiology, Cedars–Sinai Medical Center).
Article: Ultrasound Accelerates Transport of Recombinant Tissue Plasminogen Activator into Clots; Charles W. Francis (Ultrasound in Med & Biol. vol. 21. No. 3 pp. 419–424, 1995).
Article: Effect of External Ultrasound Frequency on Thrombus Disruption in Vitro; Huai Lu; et al (Journal of Thrombosis and Thrombolysis 1996).
Article: Transcutaneous Ultrasound Augments Lysis of Arterial Thrombi in Vivo; Huai Luo, MD, et al (Division of Cardiology, Cedars–Sinai Medical Center).
Article: Enhancement of the Thrombolysis in Vivo without skin and Soft Tissue Damage by Transcutaneous Ultrasound Huai Luo et al (Thrombosis Research).
Article: Dissolution of Thrombotic Arterial Occlusion by High Intensity, Low Frequency Ultrasound and Dodecafluropentant Emulsion: An in Vitro and in Vivo study; Toshihiko Nishioka et al. (Experimintal Sutdies—From Division of Health Control Medicine.
Article: Nonenvasive in Vivo Clot Dissolution Without a Thrombolytic Drug; Yochai Birnbaum, MD (Divisions of Cardiology and Antomic Pathology, Cedars–Sinai Medical Center).
Article: Enhancement of Throumolysis in Vivo Without Skin and Soft Tissue Damage by Transcutaneous Ultrasound; Huai Luo, et al (Thrombosis Research).
Abstract: Ultrasound Enhancement of Rabbit Femoral Artery Thrombolysis; Riggs PN: Francis, et al; (Cardiovasc Surg, 5(2):201–7 Apr. 1997).
Article: Low–Frequency Ultrasound Penetrates the Cranium NAD Enhances Thrombolysis in Vitro; MAsahiko Akiyama, M.D. et al (Technique Assessments).

(List continued on next page.)

*Primary Examiner*—Henry Bennett
*Assistant Examiner*—Sabrina Dagostino
(74) *Attorney, Agent, or Firm*—Walter A. Hackler

(57) ABSTRACT

A system method for sono-thrombolysis is provided employing real-time, continuous intensity and temperature monitoring. The method generally includes the steps of establishing an ultrasound delivery column to the patient being treated for a thrombotic or embolic occlusion wherein the column includes an ultrasound transducer, a coupling medium and a hydrophone. The transducer is operated in a conventional manner to deliver ultrasound to the occlusion. During operation of the transducer, characteristics of the ultrasound being delivered to the occlusion are monitored on a real-time basis with the hydrophone. In addition, the methods includes monitoring temperature proximate the site of the occlusion, the temperature also being monitored on a real-time basis. Importantly, in response to the monitored characteristics of the ultrasound, intensity of the delivered ultrasound is controlled to be maintained within a desired intensity range.

22 Claims, 2 Drawing Sheets

OTHER PUBLICATIONS

Article: Low–Frequency, Low–Intensity Ultrasound Accelerates Thrombolysis through the Skull; Stephan Behrens, et al (Ultrasound in Med and Voil. vol. 25, No. 2 pp 269–273, 1999).

Correspondence: Trans–Skull Ultrasound Therapy: The Feasibility of Using Image–Derived Skull Thickness Information to Correct the Phase Distortion; Kullervo Hynynen (IEEE Transactions on Ultrasonics, Ferroelectrics, and Frequency Control).

Review; The Sensitivity of Biological Tisse to Ultrasound; Stanley B. Barnett, et al (Ultrasound in Med. & biol., vol. 23 No. 6 pp 805–812, 1997).

Article: Enhancement of Fibrionolysis with 40–Khz Ultrasound; Valentina Suchkova, MD (Vascular Medicine Unit, Department of Medicine, University of Rochester).

Article: Effect of Ultrasound on Tissue–Type Plasminogen Activator–Induced Thrombolysis; Carl G. Lauer, MD (Department of Hematology).

ULTRASOUND SIGNAL AND TEMPERATURE MONITORING DURING SONO-THROMBOLYSIS THERAPY

The present invention generally relates to systems and methods for sono-thrombolysis and more specifically relates to systems and methods for sono-thrombolysis employing ultrasound intensity and temperature monitoring techniques.

The use of ultrasound to accelerate thrombolysis has been proposed for many years. In experimental studies, ultrasound has been used, in conjunction with thrombolytic agents to disrupt peripheral arterial and venous thrombi in animal models and to open artheroscelerotic occlusions of peripheral arteries in some patients. In early research experiments, the ultrasound was typically delivered through catheters to prevent damage to normal tissues near the site of the occlusion.

Ultrasound application has been studied for its effect in fibrinolytic therapy with a thrombolytic agent, such as a tissue-type plasminogen activator (t-PA). Studies have suggested that transcutaneous ultrasound energy, delivered in a continuous mode at high frequencies, may enhance the thrombolytic effect of some medicinal agents by promoting agitation of the clot, thereby exposing additional fibrin in the clot for binding with the medicinal agent.

Lauer et al, in *Circulation*, 1992, investigated the effects of ultrasound on t-PA induced thrombolysis both in vitro and in rabbit jugular veins. More recently, Furtuhata in the proceedings of $1^{st}$ *International Symposium of Sonodynamic Therapy*, 2000, investigated early recanalization of ischemic circulation by thrombolytic method combined with drug and ultrasound, including acceleration of thrombolysis by transcranial ultrasonic irradiation in rabbit femoral arteries and also in vitro.

The early investigators employed relatively high intensity of ultrasound at the site of exposure. Possibly, the early investigators believed that significant levels of ultrasound were needed to accomplish acceleration of lysis in both in vitro and in vivo experiments. Various methods have been used to generally assess the amount of ultrasound intensity being delivered to a site. Typically, the methods employed to assess the intensity of ultrasound used to produce results of an experiment involved sampling of intensities either before and/or after the experiment, rather than during the experiment.

Despite advances made in the field of sono-thrombolysis, there are significant problems that are not addressed by the prior art. For example, the potential for thermal injury is a significant concern that cannot be overlooked, particularly when sono-thrombolysis is employed on a human patient for treatment of an acute stroke in the brain. The present invention addresses these and other concerns and provides significant advantages over earlier sono-thrombolytic therapy methods.

SUMMARY OF THE INVENTION

Accordingly, a method for treating a patient experiencing an acute stroke, heart attack, peripheral arterial, deep vein, or other peripheral vascular occlusion using sono-thrombolysis is provided.

The present invention generally comprises establishing an ultrasound delivery column to the subject or patient, and providing real-time monitoring of both intensity and temperature in order to limit energy exposure, avoid cavitation and control heating to prevent thermal injury to the patient. Preferably, the monitoring of the ultrasound intensity and the temperature is performed continuously during application of the ultrasound. By employing careful, real-time monitoring of characteristics of the ultrasound being delivered, effective thrombolysis of the occlusion can be accomplished using low intensity ultrasound preferably in conjunction with low concentrations of thrombolytic agents.

More specifically, a method of using ultrasound to treat a patient experiencing a thrombotic or embolic occlusion, in accordance with the invention, generally comprises the steps of establishing an ultrasound delivery column to the patient, wherein the column comprises an ultrasound transducer, a coupling medium and a hydrophone, operating the transducer to deliver ultrasound to the thrombotic occlusion and monitoring ultrasound intensity on a real-time basis with the hydrophone. In response to the monitored characteristics of the ultrasound, intensity of the delivered ultrasound is controlled within a desired intensity range, using conventional electronics equipment and techniques.

The ultrasound energy is preferably provided by a ultrasound transducer assembly, utilizing, for example, a 27 kHz transducer. Preferably, pulse mode ultrasound, rather than continuous mode ultrasound, is employed for sono-thrombolysis therapy in accordance with the present invention. Preferably, the pulse mode is set at a 10% duty cycle. By using pulse mode ultrasound, average intensity delivered is reduced in comparison to levels that would be delivered using continuous mode ultrasound. The efficacy of pulse mode versus continuous mode is higher per unit of intensity delivered. Therefore, pulse mode is more desirable in terms of efficiency. Pulse average intensity is the time averaged intensity, in watts per square centimeters, during the ultrasound pulse. Temporal average intensity is the pulse average intensity multiplied by the pulse length, and divided by the time between pulses.

The desired intensity of the ultrasound preferably has a pulse average intensity of up to about 1 watt/cm. More preferably, the ultrasound has a temporal average intensity of about 0.25 w/cm$^2$ and the ultrasound intensity range may be a range of between about 0.06 w/cm$^2$ and about 0.25 w/cm$^2$ temporal average intensity. At these relatively low levels of ultrasound energy, infarction volumes of patients who are experiencing an acute stroke can be significantly reduced as will be described hereinafter.

It is noted that the actual intensity of ultrasound being delivered to the patient is influenced by many factors. For example, small variations in the contact surface (i.e. contours or shape of the body surface of the patient on which the transducer is positioned), the viscosity and entrapped air of the coupling medium, the force being applied to the transducer to ensure good contact between the transducer and the patient, all can cause significant variations in the intensity of ultrasound being delivered.

Ideally, in accordance with the invention, the hydrophone is positioned between the transducer and the subject in order to provide accurate measurement of ultrasound intensity as the energy enters the subject. Characteristics of the ultrasound can be viewed by means of a conventional oscilloscope assembly connected to the hydrophone. Intensity of the ultrasound can be adjusted by the operating technician to ensure the intensity remains within the desired range (e.g. between about 0.06 w/cm$^2$ and about 0.25 w/cm$^2$). Actual oscillographic plots of intensity may show a waveform with occasional spikes that are attributable to the presence of cavitation occurring at the site of exposure. High levels of cavitation at the site of exposure may cause excessive heating of the patient and therefor should be minimized.

Preferably, therefore, the coupling medium used should be selected to reduce or minimize the occurrence of cavitation. Specifically, in accordance with the present invention, the coupling medium may comprise a silicone material, and a thin layer of glycerine on either side thereof. Even more specifically, the hydrophone is preferably encased within a silicone material, for example a pellet of silicone material. To provide sufficient coupling, a thin layer of glycerin is placed on either side of the silicone pellet having the hydrophone encased therein. The silicone pellet and thin layer of glycerin is positioned between the transducer and the body surface of the patient. It has been found that when silicone and glycerin are used in this manner as the coupling medium, cavitation is reduced, in comparison to other more conventional coupling media such as the medium known as "Sonigel".

Temperature rise is a significant concern, especially for patients exposed to ultrasound who are experiencing an acute stroke. Hypothermia has been proposed as a method to reduce damage caused by an acute stroke. Ideally, in accordance with the present invention, the application of the ultrasound would have no effect on temperature rise of the exposed patient. Practically, a temperature rise of about 1 deg C. to about 2 deg C. may be tolerated, but no greater. In a highly advantageous embodiment of the invention, the method further comprising the step of monitoring temperature of the patient on a real-time basis, wherein the temperature is monitored proximate the site of the occlusion. This embodiment of the present invention therefor includes the step of monitoring temperature on a real time basis.

This feature of the present invention is particularly important when the method is employed for treatment of a patient experiencing an acute stroke. The step of monitoring temperature may include placing a temperature probe external to the skull of the patient, with the hydrophone in the silicone material. Temperature can be monitored on a real time, continuous basis for the purpose of limiting temperature rise and avoiding damage to the brain of a patient undergoing an acute stroke.

BRIEF DESCRIPTION OF THE DRAWINGS

The objects and advantages of the present invention will be more clearly understood and appreciated with reference to the following detailed description when considered in conjunction with the appended drawings of which.

DETAILED DESCRIPTION

Figure 1:
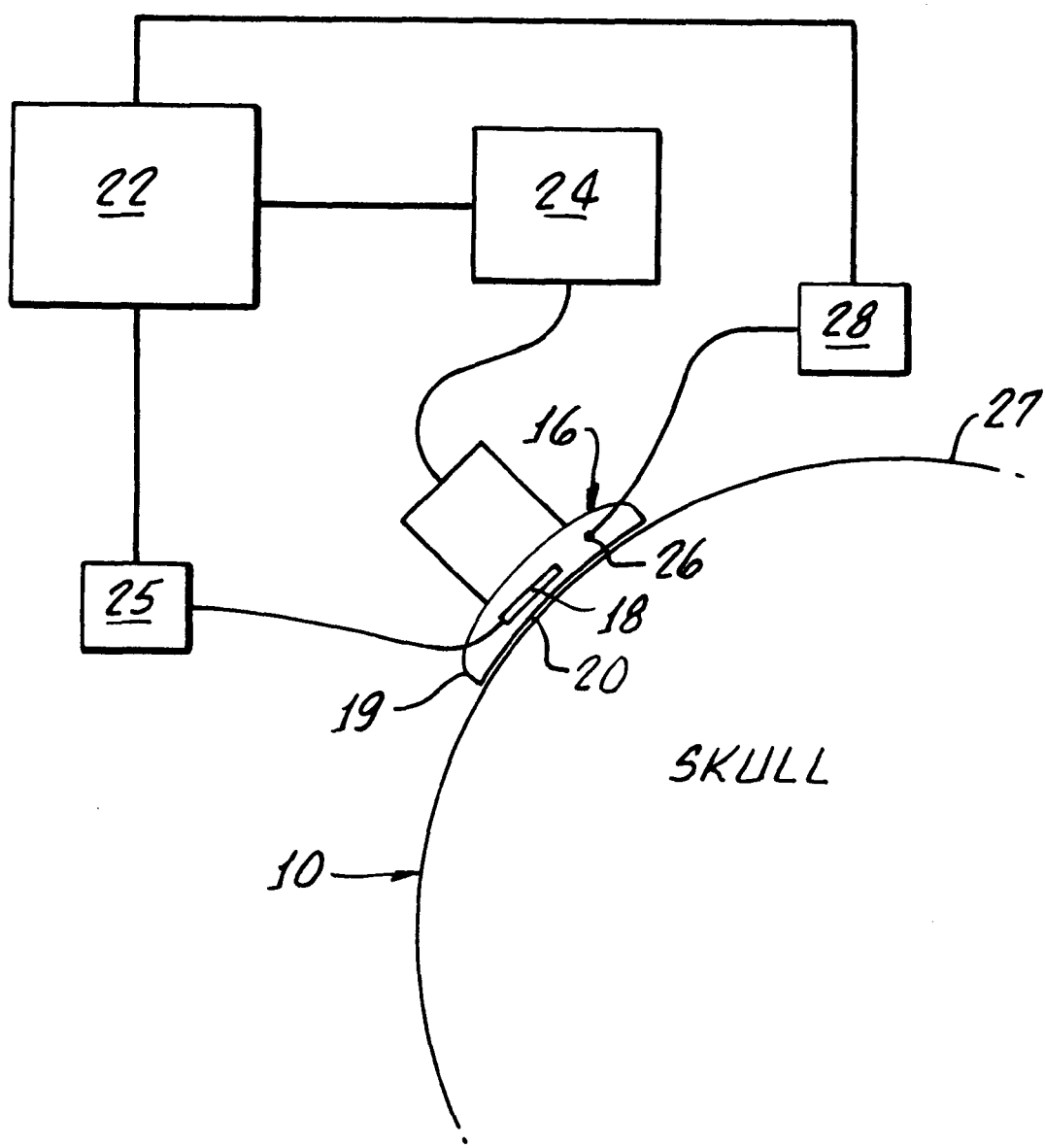
FIG. 1 shows a schematic representation of ultrasound signal and intensity monitoring system for sono-thrombolysis therapy in accordance with a method of the present invention.

Turning now to FIG. 1, a method for sono-thrombolysis therapy employing ultrasound intensity and temperature monitoring in accordance with the present invention generally comprises the steps of establishing a ultrasound delivery column to the patient 10, the column comprising an ultrasound transducer 14, a coupling medium 16 and a hydrophone 18, and operating the transducer 14 to deliver ultrasound to a thrombotic occlusion (not shown) in the patient 10. Importantly, the invention further comprises monitoring characteristics of the ultrasound being delivered to the thrombotic occlusion on a real-time basis with the hydrophone 18, and in response to the monitored characteristics of the ultrasound, controlling intensity of the delivered ultrasound within a desired intensity range. Controlling the ultrasound intensity being delivered into the patient, as needed and in response to real-time monitoring, enables the physician or technician to limit energy exposure of the patient, prevent excess heating of tissue, and ensure efficient thrombolysis of the occlusion. Characteristics of the ultrasound being delivered, such as intensity, frequency, presence of spikes (which may indicate cavitation) may be displayed as a waveform on a monitor of a conventional oscilloscope 22, or other monitoring assembly.

It has been found that careful monitoring of the acoustic field on a real-time basis, in accordance with the present invention, is essential in making a determination of the actual ultrasound intensity being delivered into the patient, to avoid exposing either too much or too little ultrasound intensity to the patient.

The present invention was generally developed for sono-thrombolytic treatment of a patient undergoing an acute stroke. Therefore, the following description will primarily refer to embodiments of the invention suitable for treatment of a patient experiencing an acute stroke. However, it is to be appreciate that the present invention should not be considered as limited thereby. As will be appreciated by those skilled in the art, with appropriate modification, the present invention may be adapted for the treatment of heart attack, occlusions occurring in deep veins and other peripheral vessels.

In accordance with one embodiment of the present invention, a method is provided for treating a patient experiencing symptoms of acute cerebral ischema, particularly along the distribution of the internal carotid artery (ICA). More specifically, the step of operating the transducer to deliver ultrasound includes insonating the Sylvian fissure region of the brain with the ultrasound beam.

Based on angiography studies, post-mortem studies, transcranial Doppler, magnetic resonance imaging, computerized tomography and other studies, it has been determined that middle cerebral artery (MCA) occlusions can be found in approximately 50% to 60% of patients, with the majority of occlusions involving the M1 and M2 segments, the M1 being occluded more often and quite consistently. The M3 segment is occluded in approximately 10% to 15% of cases. Intracranial (superclinoid) ICA occlusions are detected in approximately 5% of cases. Anterior cerebral artery (ACA) occlusions are found either alone or in association with MCA. Solitary ACA occlusions account for about 1% of all cases. Internal carotid artery extracranial occlusion or severe stenosis is present in approximately 25% of all cases. In the majority of these patients, there is an associated MCA occlusion. In approximately 20% to 25% of patients, the acute angiogram shows no evidence of an occlusion. These patients are not candidates for thrombolysis. In approximately 5% of cases, angiography shows ICA thrombosis extending intracranially, "slow flow" or other findings. These patients may not be candidates for ultrasonic thrombolysis.

In accordance with the invention, the step of insonating the Sylvian fissure region of the brain and the bifurcation of the ICA into MCA and ACA, will help lyse emboli causing approximately 45% to 55% of ICA distribution infarcts, which constituting approximately 75% to 80% of all patients eligible for t-PA or pro-urokinase medicinal therapy. The ultrasound beam will reach the supraclinoid ICA, MCA M1 and (proximal) M2 segments and ACA A1 segment. Transcranial Doppler, magnetic resonance angiography or computerized tomographic angiography studies can identify the presence of occlusion in these arterial segments.

It is noted that more distal MCA branch occlusions are not as common and will be missed by this approach. However, these emboli may respond to t-PA or pro-urokinase treatment alone and may not require additional ultrasonically accelerated thrombolysis. In these cases, routine insonation of the artery of interest, for example intermittently, may be performed.

Preferably, the step of controlling the ultrasound intensity includes maintaining the temporal average intensity within a range of between about 0.06 w/cm$^2$ and about 0.25 w/cm$^2$, with a pulse average intensity of less than about 1 watt/cm$^2$ and a temporal average intensity of about 0.25 w/cm$^2$ The ultrasound transducer may be powered by a conventional power generator assembly 24 and ultrasound intensity may be maintained within this range using conventional techniques. The ultrasound energy is preferably delivered at a low frequency, for example a frequency of less than about 100 kHz and more preferably at a frequency of about 27 kHz. Advantageously, it has been found that at about 27 kHz, attenuation of the ultrasound through the skull has been identified at approximately 1–3 db. Therefore, there is little attenuation loss and the applied external intensity exposure that is required, and the desired internal intensity are approximately the same.

Preferably, the step of delivering ultrasound comprises delivering pulsed ultrasound rather than continuous ultrasound. Pulsed ultrasound is delivered to reduce total intensity to levels below that which would be delivered by continuous ultrasound. The ultrasound is preferably delivered at a 10% duty cycle (i.e. time period on/time period off), or less. It is anticipated that results may be favorable even using pulsed ultrasound with a duty cycle of about 1%.

Preferably, the hydrophone 18 is encased in the coupling medium 16. Although any suitable coupling medium may be used, for example glycerin alone, the coupling medium 16 is more preferably silicone in conjunction with glycerin. Even more preferably, the coupling medium 16 comprises a silicone pellet 19 having a thin layer 20 of glycerin 20 applied thereto. In comparison to other coupling media such as sonigel for example, glycerin enhances whetting of a surface to which it is applied. The glycerin layer 20 may comprise no more than a fine coating of glycerin, or a glycerin film, on either side of the silicone pellet 19. The thin layer 20 is substantially held together and in place by surface tension and will not undesirably leak or flow. Advantageously, unlike a thick layer of glycerin alone, or a layer of sonigel, the thin layer 20 of glycerin will not undergo substantial levels of cavitation as a result of the ultrasound energy being radiated therethrough.

The present invention may be used to treat a patient in conjunction with medicinal therapy treatment. For example, at a t-PA concentration of 1 microgram per ml applied proximate the occlusion, the ultrasound treatment method in accordance with the invention will boost the action of the t-PA significantly. In one embodiment of the invention, the method includes delivering a thrombolytic agent proximate the occlusion.

The hydrophone signal is passed through an appropriate amplifier and filter circuitry 25 and to the oscillator 22.

Preferably, the method of the present invention further comprises the steps of monitoring temperature of the patient 10 on a real-time basis, wherein the temperature is monitored proximate the site of the occlusion.

In stroke therapy, in which the occlusion being treated is within the brain of the patient, an ultrasound beam from the transducer 14 is insonated into the Sylvian fissure region and the bifurcation of the step of monitoring temperature may be accomplished by a placing a temperature probe 26 in the coupling medium 16, or alternatively a needle thermocouple (not shown) external to the skull 27 of the patient 10. Importantly, the temperature probe, or sensor, 26 can indicate occurrence of cavitation due to associated temperature rise.

As shown, the temperature signal is passed through a thermocouple amplifier 28 and to the oscilloscope 22 for monitoring the temperature on a real-time, continuous basis.

In response to the monitored temperature, the ultrasound energy being delivered can be adjusted so as to limit any temperature rise to a safe and acceptable level. Preferably, the temperature rise is limited to an increase of less than about 2 deg C., and even more preferably, to an increase of less than about one deg C.

In addition to ultrasound intensity, monitoring the acoustic field in the ultrasound delivery column allows for the detection of cavitation. Cavitation will appear with higher and lower harmonics on the pressure waveform as displayed on the monitor. Excessive cavitation in the coupling medium can cause excessive heating, resulting in injury to the skin of the patient as well as damage to the brain beneath the skull bone.

In VITRO Studies of Ultrasound and Fibrinolusis

During development of the present invention, a series of in vitro experiments was performed to examine the effects of ultrasound at three frequencies, i.e. 27, 37 and 100 kHz, on t-PA mediated fibrinolysis, with additional variables of time, intensity and duty cycle.

In these experiments, clots were incubated with t-PA and exposed to specified, variable, ultrasound fields, and the extent of fibrinolysis was determined. In all cases, fibrinolysis was quantified by incorporating radio-labeled fibrin into the clot and measuring solubilization of radio-label as the measure of fibrinolysis. Controls included clots incubated in the same fashion without exposure to t-PA or ultrasound and clots exposed to ultrasound and without t-PA. Additional clots were incubated with t-PA alone to assess the extent of fibrinolysis in the absence of ultrasound. The important parameter for consideration is the increase in the amount of fibrinolysis with t-PA plus ultrasound in comparison with t-PA alone. The experimental apparatus comprised a water tank with an ultrasound transducer mounted on one side. Clots of platelet poor plasma were formed in test tubes and overlayed with plasma containing t-PA. A series of up to ten test tubes containing clots were rotated in the near field of the ultrasound transducer. The ultrasound field was carefully monitored and its characteristics described separately herein. Unless otherwise specified, the concentration was 1 mcg/ml in the plasma.

One series of experiments measured the extent of fibrinolysis at one hour with exposure to ultrasound at 27, 37, and 100 kHz at increasing intensities up to 1 W/cm$^2$. These experiments have shown an intensity dependent increase in fibrinolysis at all frequencies. There was approximately a three fold increase in fibrinolysis at 1 W/cm$^2$ compared to t-PA with no ultrasound. There was little difference in the results with the three frequencies tested.

Similar experiments conducted added the additional variable of time. The results were confirmatory, showing that fibrinolysis increased with time, and fibrinolysis was accelerated as a function of ultrasound intensity at all three frequencies tested.

A third set of experiments fixed ultrasound intensity and examined fibrinolysis of t-PA concentration using transducers at 27, 37 and 100 kHz. In all cases, the extent of fibrinolysis was directly related to t-PA concentration and was increased in the presence of ultrasound. The implication is that an equivalent degree of fibrinolysis can be achieved at lower t-PA concentration in the presence of ultrasound than in the absence of ultrasound. This may be important in minimizing bleeding complications which have been shown to be greater at higher t-PA concentrations.

The final experiments considered the role of duty cycle in fibrinolysis. In all cases, ultrasound enhancement of fibrinolysis was greater at higher duty cycles, with the maximum effect at 100%. There was, however a surprisingly large effect at lower duty cycles. This was particularly explored at 27 kHZ, and 10% duty cycle as a function of intensity. This shows a significant enhancement of fibrinolysis at an intensity as low as 0.25W/cm$^2$ with a 10% duty cycle. Ultrasound enhancement, however, increased up to 1 W/cm$^2$. These experiments clearly demonstrate that lower duty cycles provide relatively greater amounts of fibrinolytic enhancement than predicted based on the expected linear increase with increased duty cycle.

In summary, the data indicate that fibrinolysis is significantly enhanced with either 27, 37 or 100 kHz ultrasound. The results with t-PA concentration are those expected based on prior experiments and indicate that equivalent degrees of fibrinolysis can be achieved in the presence of ultrasound using substantially lower t-PA concentration. The intensity dependence of the fibrinolytic enhancement indicates that significant acceleration of fibrinolysis may be expected using an intensity as low as 0.25 W/cm$^2$. This represents the "maximum" intensity, and measurements demonstrate that the actual intensity to which the clot is exposed is substantially less. Thus, this offers the possibility of an important therapeutic effect at a very low intensity. The pulsing experiments surprisingly indicate that a duty cycle as low as 10% can provide considerable enhancement of fibrinolysis. The implications of this for in vivo and clinical studies are clear as the total ultrasound exposure could be minimized using appropriate pulsing.

Methods and Materials

Three source transducers (Cybersonics Inc., Erie, Pa.) operating at 27, 37 and 100 kHz, each with and active interface of approximately 3 cm, were used in the investigation. The transducers were driven by a broad band, linear amplifier (Electronic Navigation Instruments, Rochester, N.Y.). Sound fields were measured with a calibrated hydrophone, available from Bruel and Kjer, Copenhagen, Sweden. The response of the hydrophone was approximately independent of frequency at the frequencies of interest. Waveforms were approximately sinusoidal except at the highest output levels where minor instabilities were frequently observed. These minor instabilities may have resulted from the occurrence of cavitation.

Clot lysis experiments were performed in thin-walled, 8 mm diameter, nitrocellulose tubes, available from Beckman Instruments, Inc., Palo Alto, Calif. The tubes were sealed and placed in a circular test tube rack with a diameter of 2.5 cm holding 8 tubes. The rack was immersed in a tank of degassed water maintained at a temperature of 37° and the rack was rotated at approximately 8 turns per minute throughout the exposure period. The source transducers were mounted in the wall of the tank and the rack positioned so that the clots within the tubes passed approximately 1 cm from the face of the transducer during rotation.

Sound fields decreased rapidly with distance from the sources particularly at the two lowest frequencies. As a result, the exposure of individual clots varied with position and time as the rack was rotated. To characterize the actual exposures received by the clots, the Bruel and Kjer hydrophone was substituted for one of the tubes in the rack and the field measured as a function of position of the rack. At the two lower frequencies the temporal average intensities during rotation were approximately one quarter of the reported maximum intensity (0°). At 100 kHz, the temporal average intensity was slightly greater than one half of the reported maximum intensity.

In addition, to show variation in intensity resulting from tube rotation, certain experiments were conducted with pulsed sound fields. In each case the pulse repetition frequency was approximately 70 Hz, with a pulse period of about 14 ms. Duty cycle was varied via the pulse length. For example, for a 50% duty cycle, the pulse length was approximately 7 ms; for a 10% duty cycle, the pulse length was approximately 1.5 ms. At the two lower frequencies, the time for the pulse to reach full amplitude was approximately about 0.3 ms. To achieve an effective 10% duty cycle, the drive time of the transducer was about 2 ms. The 100 kHz transducer required approximately 1.5 ms to reach steady state conditions. Hence, at a 10% duty cycle, the pulse reached full amplitude at approximately the time that the driving signal ceased. A few exploratory experiments were carried out with a 1% duty cycle. In that case, the maximum amplitude reached during the pulse were roughly one half the steady state amplitude.

Ex VIVO Skull Studies

During tests conducted related to the development of the present invention, for the effectiveness of ultrasound application for the treatment of stroke, ultrasound bone transmission, heating and bioeffects were studied. The purpose of one such experiment was to assess the ultrasound parameters that are driving conditions to cause the desired heating caused by exposure to ultrasound in vivo in rats. In one such test, measurements of heating in a rat skull during exposure to ultrasound at 27 kHz with a horn transducer were taken. Examples are shown in Tables 1 and 2 below. Temperature rises reported in these tables result from an exposure duration of 250 sec.

TABLE 1

Live Rat: thermocouple in brain: water coupling

| Pulse average intensity | Temporal average intensity | Temperature rise (° C.) |
|---|---|---|
| 0.5 | 0.24 | 0.7 |
| 1 | 0.24 | 0.7 |
| 2 | 0.2 | 0.7 |
| 2 | 1 | 4.1 |

TABLE 2

Dead Rat: thermocouple in brain: silicone plus glycerin coupling

| Pulse average intensity | Temporal average intensity | Temperature rise (° C.) |
|---|---|---|
| 0.27 | 0.27 | 2.5 |
| 0.5 | 0.23 | 1.6 |
| 1 | 0.27 | 1.8 |
| 1 | 0.5 | 4.0 |

From these examples, it is evident that the temperature rises associated with exposure of the rat skull can be significant. Generally, the temperature rise appears to be proportional to the temporal average intensity of the exposure. However, it should be noted that for these measurements, intensity was not measured during the exposure. Rather, the transducer was calibrated prior to exposure by coupling the hydrophone to a rubber absorber. From these preliminary experiments, an estimate of the temperature rise for a 250 s exposure with a temporal average intensity of about 0.25 W/cm$^2$ is about 1° C. Similar results were obtained for measurements of temperature rise in a severed rat head with the thermocouple threaded just below the scalp.

The medium used to couple the transducer to the rat head has been found to effect the temperature rise. This may result because one medium enhances coupling of sound to the skull and/or cavitation is enhanced in some coupling media. It is known that bubbles trapped in sonigel readily cavitate which could result in a more significant temperature rise than other media, such as the silicone/glycerin arrangement used in accordance with the present invention.+

Preferably, in accordance with the present invention, the coupling medium comprises silicone used in conjunction with glycerin. More specifically, a pellet of silicone is provided with a relatively thinner layer of glycerin applied thereto.

All measurements reported in the above tables were performed with the transducer and skull in air with a coupling medium comprising glycerin between the skull and the transducer. In addition to the possibility of heat generation via cavitation in the coupling medium as described above, the confinement of the sound field within the skull (i.e. no exit path) may contribute to enhanced heating.

Temperature Ranging Studies

In other experiments conducted during development and practice of the present invention, ultrasound exposure and monitoring processes were studied on the Wistar rat brain. These experiments were conducted to assure that the predictions of the temperature rise made in the ex vivo skull studies described hereinabove, were validated in live, stroked rats. In addition, a comparison was made between continuous wave ultrasound and pulsed wave ultrasound at the same level of temporal average intensity (i.e. 0.25 W/cm$^2$)

Prior to the study of the stroked rats, an assessment was performed to validate the temporalis method of monitoring brain temperature. Three non-stroked rats (A, B and C) were exposed to ultrasound with a thermocouple planted in the brain, and with a temperature probe in the temporalis muscle. The purpose of the assessment was to compare the results of two methods of temperature monitoring, i.e. invasive (thermocouple in brain) and non-invasive (thermocouple in temporalis muscle).

Results of the invasive versus non-invasive comparison assessment are summarized as follows. Non-invasive values of temperature rise were typically smaller than invasive values. However, the difference was consistently one deg C. or less. Non-invasive values accurately reflected the trend of the invasive values. For animals B and C, the total temperature rise over about 60 minutes was 0.8 deg C. and 1.5 deg C. respectively, accurately measured by the non-invasive method.

Figure 2:
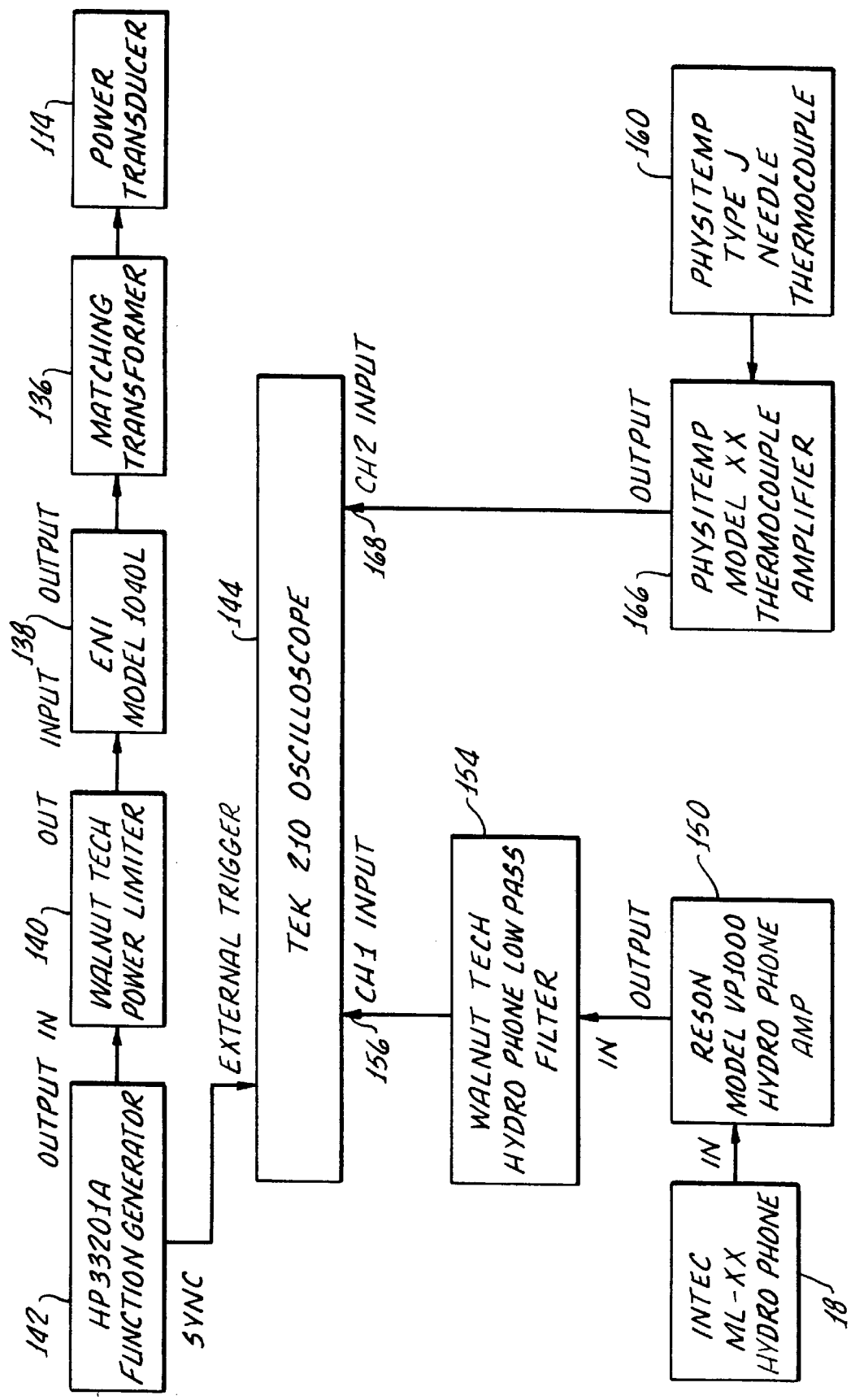
FIG. 2 shows a block diagram an ultrasound apparatus used for performing the method of the present invention.

Referring specifically to FIG. 2, an ultrasound system connection diagram is shown that was used in practice of the present invention on stroked rat subjects.

Ultrasound energy was radiated into the subject (not shown) by means of a 26 kHz ultrasound transducer 114 with a 1 cm diameter end piece (Cybersonics, Erie, Pa.). The transducer 114 is shown connected to a matching transformer 136, a power amplifier 138 (model 1040L available from ENI Corp., Rochester, N.Y.), a power limiter 140 and a signal function generator 42 (model no. 33120a, available from Hewlett Packard, Palo Alto, Calif.). The signal function generator 142 is shown connected to oscilloscope 144 (model no. TDS 210, available from Tektronix Corp., U.S.A.). A signal from hydrophone 18 (model no. ML-XX available from INTEC Research, Sunnyvale, Calif.) was passed through a hydrophone amplifier 150 (model no. VP 1000 available from Reson, Inc, U.S.A.), through a hydrophone low pass filter circuit 154 (such as available from Walnut Technologies, Boston, Mass., and having model no. XXS/NYY) and to an input channel 156 of the oscilloscope 144. For temperature monitoring on a real-time basis, a needle type thermocouple 160 was used (model no.BAT-12 thermocouple, available from Physitemp Instruments Corp., U.S.A.), connected to a thermocouple amplifier 166 and to a second input channel 168 of the oscilloscope 144.

Although there has been hereinabove described a method for ultrasound signal and intensity monitoring during sonothrombolysis therapy, in accordance with the present invention, for the purpose of illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defined in the appended claims.

What is claimed is:

1. A method of using ultrasound to treat a patient experiencing a thrombotic or embolic occlusion, the method comprising the steps of:

establishing an ultrasound delivery column to the patient, the column comprising an ultrasound transducer, a coupling medium and a hydrophone;

operating the transducer to deliver ultrasound to the occlusion;

monitoring characteristics of the ultrasound being delivered to the occlusion on a real-time basis with the hydrophone; and in response to the monitored characteristics of the ultrasound, controlling intensity of the delivered ultrasound within a desired intensity range.

2. The method according to claim 1 wherein the desired intensity range has a pulse average intensity of about 1 watt/cm$^2$.

3. The method according to claim 1 wherein the desired intensity range has a temporal average intensity of about 0.25 w/cm$^2$.

4. The method according to claim 1 wherein the desired intensity range is a temporal average range of between about 0.06 w/cm$^2$ and about 0.25 w/cm$^2$.

5. The method according to claim 1 wherein the step of delivering ultrasound comprises delivering pulsed ultrasound.

6. The method according to claim 5 wherein the pulsed ultrasound is delivered with a 10% duty cycle.

7. The method according to claim 1 wherein the transducer delivers ultrasound at frequency of less than about 100 kHz.

8. The method according to claim 1 further comprising delivering a thrombolytic agent into the site of the occlusion.

9. The method according to claim 1 wherein the step of monitoring characteristics is performed using a hydrophone positioned between the transducer and the patient.

10. The method according to claim 9 wherein hydrophone is encased in the coupling medium.

11. The method according to claim 10 wherein the coupling medium is comprised of a silicone material.

12. The method according to claim 1 further comprising the steps of monitoring temperature of the patient on a real-time basis, wherein the temperature is monitored proximate the site of the occlusion.

13. The method according to claim 12 wherein the occlusion being treated is within the brain of the patient.

14. The method according to claim 12 further comprising the step of, in response to the monitored temperature, controlling a rise in temperature to less than about 2 deg C.

15. The method according to claim 12 further comprising the step of, in response to the monitored temperature, controlling a rise in temperature to less than about 1 deg C.

16. The method according to claim 1 wherein the step of monitoring characteristics of the ultrasound includes monitoring the presence of cavitation in the coupling medium.

17. A method of using sono-thrombolysis for treatment of a patient experiencing a thrombotic or embolic occlusion in the brain, the method comprising the steps of:

establishing an ultrasound delivery column to the patient, the column comprising an ultrasound transducer, a coupling medium and a hydrophone;

operating the transducer to deliver ultrasound to the occlusion;

monitoring characteristics of the ultrasound being delivered to the occlusion on a real-time basis with the hydrophone;

monitoring temperature proximate the site of the occlusion, the temperature being monitored on a real-time basis; and in response to the monitored characteristics of the ultrasound, controlling intensity of the delivered ultrasound within a desired intensity range.

18. The method according to claim 17 wherein the step of monitoring temperature includes placing a temperature probe in a non-invasive location with respect to the skull of the patient.

19. The method according to claim 17 further comprising the step of, in response to the monitored temperature, controlling a rise in temperature to less than about 2 deg C.

20. The method according to claim 17 further comprising the step of, in response to the monitored temperature, controlling a rise in temperature to less than about 1 deg C.

21. The method according to claim 17 wherein the step of monitoring characteristics of the ultrasound includes monitoring the presence of cavitation in the coupling medium.

22. The method according to claim 17 further comprising delivering a dose of a thrombolytic agent proximate the occlusion.

* * * * *